United States Patent [19]

Humphrey

[11] Patent Number: 5,458,614
[45] Date of Patent: Oct. 17, 1995

[54] AUGMENTED POLYMERIC HYPODERMIC DEVICES

[76] Inventor: Bruce H. Humphrey, P.O. Box 07513, Milwaukee, Wis. 53207

[21] Appl. No.: 117,231

[22] Filed: Sep. 3, 1993

Related U.S. Application Data

[63] Continuation-in-part of Ser. No. 754,457, Sep. 3, 1991, abandoned.

[51] Int. Cl.⁶ ............................. A61M 5/00; A61M 5/31
[52] U.S. Cl. ...................... 604/239; 604/272; 604/198; 604/192; 606/182; 606/181
[58] Field of Search ...................... 606/181, 167, 606/182, 183; 604/272, 236, 264, 158, 239, 192, 199, 198; 128/770, 771

[56] References Cited

U.S. PATENT DOCUMENTS

| | | | |
|---|---|---|---|
| 4,360,016 | 11/1982 | Sarrine | 128/763 |
| 4,375,815 | 3/1983 | Burns | 606/182 |
| 4,416,279 | 11/1983 | Lindner et al. | 606/182 |
| 4,838,877 | 6/1989 | Massau | 604/272 |
| 4,858,607 | 8/1989 | Jordan et al. | 606/182 |
| 4,929,237 | 5/1990 | Medway | 604/198 |
| 4,957,488 | 9/1990 | Cameron et al. | 604/161 |

FOREIGN PATENT DOCUMENTS 0160468   10/1982   Japan ................... 604/272

*Primary Examiner*—C. Fred Rosenbaum
*Assistant Examiner*—V. Alexander

[57] ABSTRACT

This invention relates to augmented polymeric hypodermic needles and lancets. A flexible polymeric hypodermic needle or lancet is stiffened and made to more readily pierce the skin by working in conjunction with an augmenting structure. The devices are by their nature safer than present metal hypodermic needles or lancets. "Anti-stick", one-time use, and safety shielded models are demonstrated. Novel manufacturing methods will lead to devices that are less expensive than their metal counterparts. Unlike metal hypodermic devices these can be easily incinerated. This invention makes possible safe, easy to use, low cost, disposable hypodermic devices for injection, blood sampling and testing.

10 Claims, 4 Drawing Sheets

AUGMENTED POLYMERIC HYPODERMIC DEVICES

RELATED APPLICATION

This application is a Continuation-in-Part Application of U.S. patent application Ser. No. 07/754,457 filed Sep. 3, 1991, now abandoned.

BACKGROUND OF THE INVENTION

1. Field of the Invention

This invention generally relates to hypodermic devices and, more particularly, is concerned with augmented polymeric hypodermic devices.

2. Description of the Prior Art

Metal hypodermic needles and lancets have not changed substantially in over 100 years. They have many disadvantages. The foremost is that they are dangerous. They are involved in the transmission of such deadly diseases as AIDS through inadvertent "needle sticks" of health care workers. Currently the risk is an unacceptable 1 in 200. In addition, the metal needles can break during use, requiring surgery to remove. Further, the metal needles and lancets are extremely difficult to destroy. Even segments or stubs of the needles and lancets are dangerous. They are not burnable by ordinary means and, thus, pose a continuing disposal and health problem.

Others have made many attempts to solve these problems. Their proposed solutions have taken two main routes. The first, is a substitution of plastic for metal in the needle material. The second, is a guard to shield the needle. Both avenues have failed for a variety of reasons. Plastic has not replaced metal because thin plastic needles that are hard enough to puncture the skin are too brittle and shatter, while more flexible needles lack the requisite stiffness to pierce the skin. Previous needle guards have proven to be either unwieldy, too costly, inconvenient to use or otherwise ineffective.

The following patents are included for reference as to the state of the prior art at the time of this application.

A plastic hypodermic needle that attempts to mimic the shape and function of a conventional metal needle is described by U.S. Pat. No. 2,512,568 to Saffir. U.S. Pat. No. 2,512,569 also to Saffir illustrates metal and other hard materials used only on the tip of the plastic needles to facilitate skin puncture, much as metal arrowheads are put on wooden shafts. U.S. Pat. No. 2,954,768 to Hamilton shows plastic needles with unusual piercing tip configurations. U.S. Pat. No. 3,831,814 to Butler shows another large plastic needle with unusual tip geometry. A plastic hypodermic needle with angled side portals is revealed by U.S. Pat. No. 4,838,877 to Massau.

A closed, triangular cross section, metal hypodermic needle is shown in U.S. Pat. No. 3,090,384 to Baldwin et al.

Spring biased shields for conventional metal needles are shown by the following U.S. Pat. Nos. 2,674,246 to Bower; 2,876,770 to White; 3,134,380 to Armao; 4,416,663 to Hall; 4,507,118 to Dent; 4,664,654 to Strauss; 4,795,432 to Karczmer; and 4,929,237 to Medway.

To guard conventional metal needles, hand operated shields which slide into different positions on the hypodermic syringe body are shown in U.S. Pat. Nos. 4,695,274 to Fox; and 4,702,738 to Spencer.

U.S. Pat. No. 3,884,230 to Wulff describes a conventional metal hypodermic needle mounted on a flexible sleeve and surrounded by a biased spring assembly for inoculating livestock.

A resilient foam rubber or plastic biased guard of a conventional metal needle is shown by U.S. Pat. No. 4,775,369 to Schwartz. U.S. Pat. No. 4,883,068 to Dechow illustrates a blood sampling device which uses resilient foam or springs for biasing and sequencing functions of conventional metal needles.

Needle sheaths for extremely long conventional metal hypodermic needles, mainly for cervical area injections, are shown in U.S. Pat. Nos. 3,356,089 to Francis; and 3,406,687 to Moyer.

No matter what the precise merits of the preceding, cited patents, none anticipates this invention.

SUMMARY OF THE INVENTION

This invention solves the problems presented by conventionally used metal hypodermic needles and lancets by augmenting polymeric hypodermic needles and lancets. A flexible polymeric hypodermic needle or lancet is stiffened and made to more readily pierce the skin by working in conjunction with an augmenting structure. The resultant augmented polymeric hypodermic devices have the following advantages:

1. They can be made in smaller diameters, resulting in less pain, without fear of breakage.

2. They can be made with conical points which create less tissue damage, again causing less pain and faster healing.

3. The needles can be made clear or light transmissive to permit the blood or medication within to be viewed.

4. They can be made with integral safety guards to lessen the spread of such deadly diseases as AIDS.

5. They are less costly to manufacture than conventional hypodermic devices.

6. Unlike metal needles and lancets, these can be destroyed or rendered harmless by incineration, thus reducing contamination and disposal problems.

Many inventions have been inspired by nature. The sticking of burrs to clothing was the inspiration for "Velcro". It can be argued that metal hypodermic needles mimic the fangs of a snake. The initial inspiration for this invention possesses the least painful skin piercer and the most efficient blood extractor in nature—the mosquito. A microscopic examination of the structure of the mosquito which actually "sucks" the blood, the stylet, reveals that it is too fragile to alone puncture the skin. It must be supported by the labium in order to function. Herein is the secret of the mosquito. To clearly illustrate the advantage of this invention over metal hypodermic devices, it is only necessary to look at their respective inspirations from nature and ask the simple question, "Which causes less pain and fear—a mosquito or a snake ?"

The polymeric hypodermic needle or lancet of this invention will not by itself readily puncture the skin. Like the stylet of the mosquito, it must be stiffened or supported by an augmenting means. The augmenting means is slidably engaged. Together, synergistically, they form augmented polymeric hypodermic devices. Together, they succeed where plastic needles alone have, in the past, failed. It must be emphasized that metal needles and lancets will pierce the skin unaided. Regardless of how many parts, be they called guards, guides or whatever, are associated with the metal needle or lancet, the needle or lancet will pierce the skin by itself.

This invention teaches new devices which will make the removal of body fluids and the injection of medicaments less painful, less costly, more safe, and the by-products easier to dispose.

DETAILED DESCRIPTION OF THE INVENTION

Figure 1:
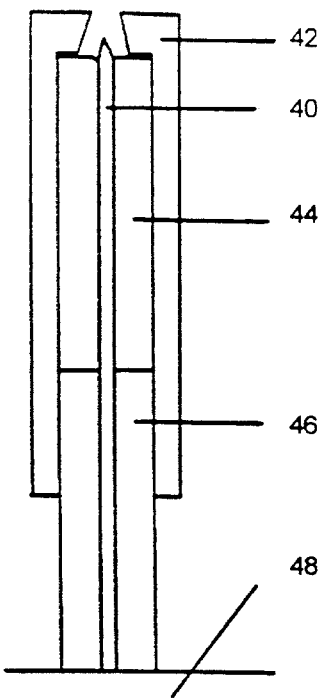
FIG. 1 is a schematical side view of the augmented polymeric hypodermic device with slidable guard and lancet.

Augmented polymeric hypodermic devices are comprised of essentially three parts: a polymeric, flexible piercing member with a piercing tip; an augmenting means to stiffen the piercing member sufficiently so that together they can perform the piercing process; and a supporting base structure to which the piercing member is attached and which supports the augmenting means.

The flexible, polymeric piercing member can be either one of two broad classes: a solid lancet; or a needle with at least one lumen. The piercing tip can be either one of three broad classes: a solid lancet tip; a hollow needle tip; or a frangibly sealed hollow needle tip. The angle of the tip can be either: flat; oblique; compound; or conical. The flexible, polymeric piercing member can be extruded from a suitable plastic such as a polycarbonate, although other polymeric materials can also be used. The plastic can be transparent or light transmissive to allow the blood or medicament within to be viewed. The plastic can be virgin, or recycled material, or it can have additives such as glass or carbon fibers for strength and hardness. All of the devices described are burnable.

The augmenting means can comprise one or more parts. All of the parts slide in relationship to the piercing member. The augmenting means is at least partly about the piercing member. The augmenting means stiffens the piercing member. It slides in relationship to the piercing member so that it can expose the piercing tip from the guarded position and allow the piercing member to complete the piercing process. The augmenting means continues to stiffen the piercing member as it slides. The augmenting means is supported by the supporting base structure.

The supporting base structure can be relatively flat or it can have one or more projections. When it is flat, then the augmenting means rests on its surface. The augmenting means can also be attached either fixedly or removably. When the supporting base structure has a projection(s) then at least one part of the augmenting means slides either on or in relation to that projection(s). The piercing member can be attached to the supporting base structure by one or a combination of several methods such as: adhesive; solvent; heat; or by molding. The supporting base structure can be very simple as in the case of a polymeric hypodermic lancet, in which the lancet is merely attached. However, the supporting base structure for the polymeric hypodermic needle can take many forms, as it is the function of the lumen(s) of the polymeric needle to transfer generally liquid material. Therefore, the supporting base structure must be of a shape that is either part of a reservoir itself or can be attached to a reservoir. A reservoir is something which can hold a generally liquid material, such as a syringe or an ampule. The reservoir does not have to be plastic. The supporting base structure can also be a means of attachment to a syringe such as a hub, a terminal end of medical tubing or any other means of attachment to a reservoir. Besides being used for injections, blood sampling and other uses for humans the devices can also find a wide use in veterinary medicine.

The following will expand on the general description stated above with a detailed explanation of the drawings.

Figure 18:
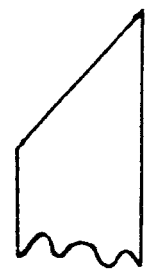
FIGS. 18 and 19 are schematical side views of different lancet tip angles.
Figure 19:

In one preferred embodiment of the device as shown in FIG. 1, the slidable guard (42) is in slidable proximity to supporting base projection (46) to which the polymeric hypodermic lancet (40) is attached. The slidable guard (42) is also in slidable relationship to the polymeric hypodermic lancet (40). The slidable resilient foam (44) restrains the sideways flexure of the polymeric hypodermic lancet (40) as it slides in relation to the lancet ,while it is itself being contained and compressed by the slidable guard (42) during the piercing process. These two, slidable guard (42) and slidable resilient foam (44) work together synergistically to make an augmenting means that makes it possible for the polymeric hypodermic lancet (40) to pierce the skin, a function that the lancet would otherwise be unable to do unaided. The supporting base projection (46) is either attached to or is an integral molded part of the supporting base structure (48). The supporting base structure (48) is here represented in its simplest form. The means of attaching the lancet to the base can be selected from any of the designs as shown in FIGS. 20 through 23. The slidable guard (42) and the supporting base structure (48) and supporting base projection (46) can be made from an inexpensive polystyrene; the polymeric hypodermic lancet (40) from a polycarbonate; and the slidable resilient foam (44) from a foam rubber or a polymeric foam such as a polyurethane. The composition of these parts is, however, not limited to the above mentioned materials. The factors which determine material selection are functionability, coupled with reasonable cost and ease of manufacture. The slidable guard (42) and the supporting base structure (48) and supporting base projection (46) can be made by injection molding; the polymeric hypodermic lancet (40) by extrusion; and the slidable resilient foam (44) by extrusion or cut from sheet stock with dies like doughnuts or it can be cut in parallelograms that are subsequently rolled and fused with heat, solvent or adhesive along one side to form a tube. The polymeric hypodermic lancet (40) is given a sharpened tip as shown in one of the FIGS. 18 or 19 by a mechanical process such as shearing or grinding, by a heat method such as a laser. The polymeric hypodermic lancet (40) is attached to the supporting base structure (48) and supporting base projection (46) by an adhesive, by solvent, or by heat, or the supporting base structure (48) and supporting base projection (46) are molded around the polymeric hypodermic lancet (40). The supporting base structure can also be molded of two or more parts and then attached to the lancet by one of the previously described methods. The supporting base projection (46) can be molded as an integral part of the supporting base structure (48) or it can be molded separately and then attached to the supporting base by heat, solvent or adhesive.

Figure 2:
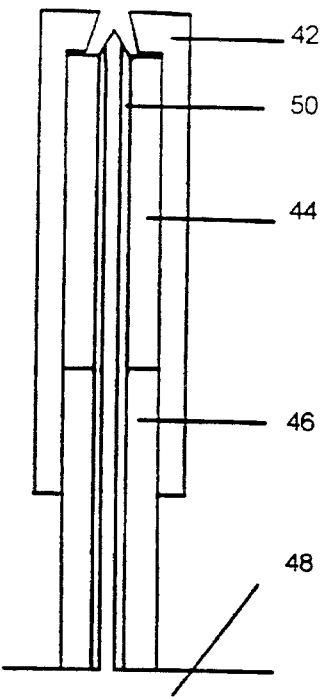
FIG. 2 is a schematical side view of the augmented polymeric hypodermic device with slidable guard and hollow needle.

FIG. 2 is identical to FIG. 1 with the exceptions that a polymeric hypodermic needle (50) with a piercing tip and at least one lumen replaces the lancet and the needle is attached to the supporting base structure (48) which has a corresponding hole so that generally fluid material can pass through. The supporting base structure is selected from one of the FIGS. 24 through 27. The supporting base structure (48) can be a hub for attaching a needle to a syringe such as a "Luer" type or one of several snap-on designs. The supporting base structure can also be an integral part of a one-piece syringe or ampule or other medical hypodermic device. The piercing tip is selected from one of the FIGS. 10 through 17, which includes the frangibly sealed tips that will be described later.

Figure 3:
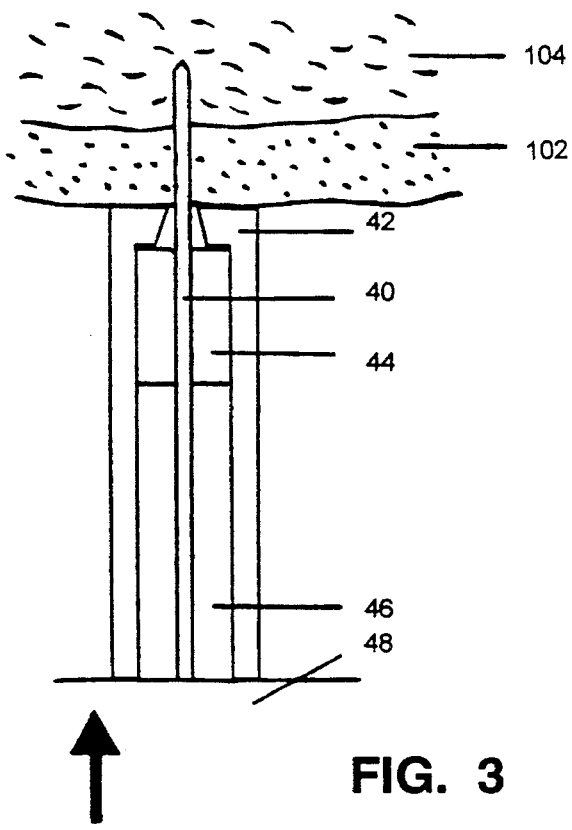
FIG. 3 is a schematical side view of the augmented polymeric hypodermic device of FIG. 1 with slidable guard and lancet in use, piercing the skin and underlying subcutaneous tissue.

In FIG. 3, the polymeric hypodermic lancet device of FIG. 1 is illustrated after completing the piercing process. Skin (102) and subcutaneous tissue (104) are shown after being pierced. During the piercing process, force is exerted—as represented by the black arrow pushing the rear of the augmented polymeric hypodermic device. This causes the slidable guard (42) to come in contact with skin (102) and then to be pushed against and compress the slidable resilient foam (44). As the polymeric hypodermic lancet (40)is pushed through skin (102) and into the subcutaneous tissue (104), the slidable resilient foam (44) restrains the sideways flexure of the lancet thereby stiffening it sufficiently to make the piercing process possible. The depth of the piercing process can be controlled by the distance that the slidable guard (42) can travel before being stopped by making contact with the supporting base structure (48). If this distance is greater, then the lancet (40) will pierce deeper. If the distance is less, then the lancet will make a shallower puncture. The slidable guard (42) is guided by and slides on the supporting base projection (46). During the piercing process the slidable resilient foam (44) is compressed between the slidable guard (42) and the supporting base projection (46). In the "at rest" position, before the piercing process begins, the slidable resilient foam (44) is not under compression so there is no tendency for the device to come apart. Friction holds the slidable guard (42) to the supporting base projection (46). After the piercing process has been completed, the device is destroyed by burning, solvents, shredding, grinding, or a combination of these simple destructive means.

It should be obvious that the piercing process for the polymeric hypodermic needle device of FIG. 2 will be the same. The only difference is that substantially liquid material can be extracted or injected through the lumen of the needle which extends through the supporting base structure (48). In the special case of the polymeric hypodermic needle device of FIG. 2 with a frangibly sealed piercing tip, after the piercing process is complete, then other pressure is exerted on the liquid material in the syringe or ampule thereby breaking the frangibly sealed piercing tip and expelling the material through the lumen of the needle into the subcutaneous tissue.

Figure 4:
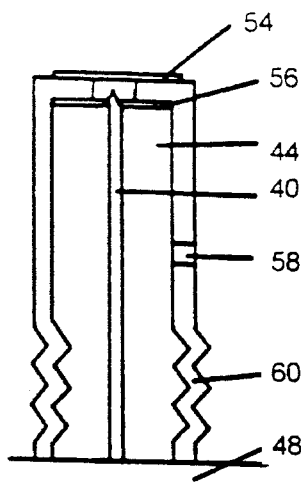
FIG. 4 is a schematical side view of the augmented polymeric hypodermic device with a slidable collapsible guard and lancet.

In another preferred embodiment of the device as shown in FIG. 4, slidable collapsible guard (60) makes a supporting base projection unnecessary, Slidable resilient foam (44) is injected through hole (58). It is restrained from oozing out by disk (56). Seal (54) provides asepsis. FIG. 4 shows the polymeric hypodermic lancet (40) model of this style. All of the lancet tip and lancet supporting base structure designs can be used with this model.

Figure 5:
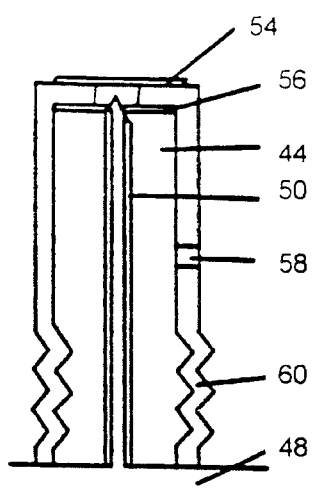
FIG. 5 is a schematical side view of the augmented polymeric hypodermic device with a slidable collapsible guard and hollow needle.

FIG. 5 shows the polymeric hypodermic needle (50) version. Again, the difference between the two models is that the polymeric hypodermic needle (50) has at least one lumen as described previously. The lumen of the needle mates with a corresponding hole in the supporting base structure. The polymeric hypodermic needle (50) of FIG. 5 can also have a frangibly sealed tip as previously described as well as any of the other needle tip and needle supporting base structure designs.

Figure 6:
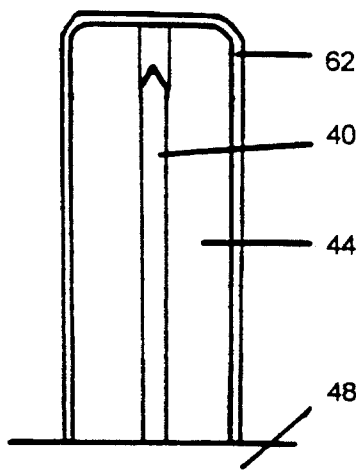
FIG. 6 is a schematical side view of the augmented polymeric hypodermic device with a slidable shrink wrap guard and lancet.

In another preferred embodiment of the device as shown in FIG. 6, slidable resilient foam (44) is held in place and asepsis is provided by slidable shrink wrap guard (62) which encloses slidable resilient foam (44) while it maintains asepsis. During the piercing process, the polymeric hypodermic lancet (40) pierces the slidable shrink wrap guard (62); the slidable resilient foam (44) is compressed thereby stiffening the polymeric hypodermic lancet (40). The slidable resilient foam (44) is made so that it extends past the end of the polymeric lancet (40) so that the slidable shrink wrap guard (62) can be placed over the slidable resilient foam (44) without being prematurely pierced by the polymeric hypodermic lancet (40). The polymeric hypodermic lancet (40) and the slidable shrink wrap guard (62) are attached to the supporting base structure (48) which supports the slidable resilient foam (44). Any of the other lancet tip and lancet supporting base structures can be employed with this model. This is one of the least expensive of the designs to manufacture. It readily lends itself to testing procedures where a one time use, easily disposable blood sampling lancet is desired.

Figure 7:
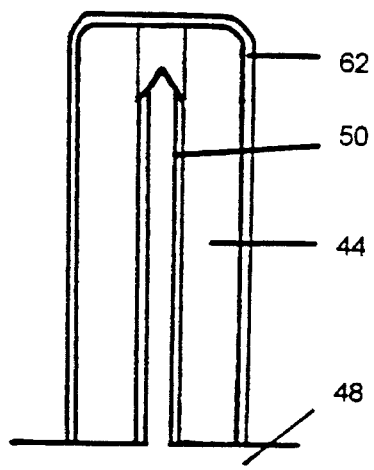
FIG. 7 is a schematical side view of the augmented polymeric hypodermic device with a slidable shrink wrap guard and hollow needle.
Figure 11:
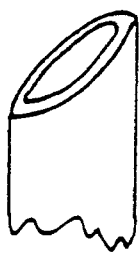
Figure 12:
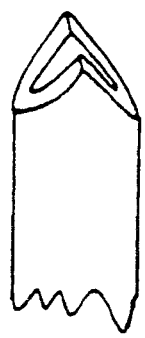

FIG. 7 illustrates the polymeric hypodermic needle (50) version of this model. The polymeric hypodermic needle (50) does not become clogged as it pierces the slidable shrink wrap guard (62), as long as the piercing tip geometry of the hollow needle design is oblique or compound as illustrated in FIGS. 11 or 12 respectively. Of course, if the piercing needle tip is selected from one of the frangibly sealed models as shown by FIGS. 13 through 17, then it can't become clogged. Again, the lumen of the needle extends through a corresponding hole in the supporting base structure. Any of the other needle tip and needle supporting base structure designs can be used with this device.

Figure 8:
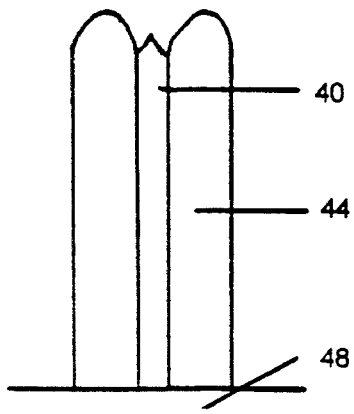
FIG. 8 is a schematical side view of the augmented polymeric hypodermic device with slidable resilient foam and lancet.

In another preferred embodiment of the device as shown in FIG. 8, slidable resilient foam (44) alone stiffens the polymeric hypodermic lancet (44). The supporting base structure (48) and the means of attaching the polymeric hypodermic lancet (40) can be selected from any of those shown in FIGS. 20 through 23. The lancet piercing tip design can be selected from those shown in FIGS. 18 and 19. This model makes a one-time use device that is inexpensive to manufacture and easy to dispose.

The design of FIG. 8 can also be made with a polymeric hypodermic needle (50) in place of the polymeric hypodermic lancet (40) and with the lumen of the needle extending through the supporting base structure (48). The supporting base structure (48) and the means of attachment of the polymeric hypodermic needle (50) can be selected from any of FIGS. 24 through 27. This design can also be made with any of the hollow needle piercing tip designs, including a frangibly sealed piercing tip, selected from FIGS. 10 through 17.

Figure 9:
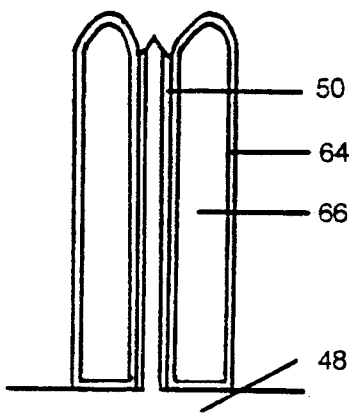
FIG. 9 is a schematical side view of the augmented polymeric hypodermic device with slidable compressible ring and hollow needle.

FIG. 9 illustrates a model with a slidable compressible ring (64) which fits like a doughnut around the polymeric hypodermic needle (50) to stiffen it during the piercing process. The polymeric hypodermic needle (50) is attached to the supporting base structure in any one of the ways shown in FIGS. 24 through 27. The piercing tip of the polymeric hypodermic needle (50) is selected from any one of the designs as shown in FIGS. 10 through 17, including the frangibly sealed tip models. The slidable compressible ring (64) is attached to the supporting base structure (48) and is made from a plastic material such as polyethylene which is at least partially filled with a material (66) which is selected from the list of: resilient foam; gas; a specific gas, such as nitrogen; liquid; a specific liquid such as distilled water. During the piercing process, the slidable compressible ring (64) is compressed thereby simultaneously exposing the piercing tip and stiffening the polymeric hypodermic needle (50). The material (66) is selected to provide support for the slidable compressible ring (64) so that the ring will compress in a controlled and predetermined manner to facilitate the piercing process.

The embodiment of FIG. 9 can also be made with a polymeric hypodermic lancet (40) in place of the needle. The supporting base structure (48) and the means of attaching the polymeric hypodermic lancet (40) can be selected from any of those shown in FIGS. 20 through 23. The piercing tip design can be selected from either one of FIGS. 18 or 19.

Figure 10:
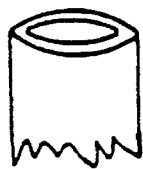
FIGS. 10 through 12 are perspective views of different tip angles of hollow needles.

FIGS. 10 through 12 show perspective views of various tip geometries for the polymeric hypodermic needle (50). The preferred embodiments are FIGS. 11 and 12, oblique and compound angles respectively. The tips are cut with a mechanical means such as shearing or grinding or laser or other heat source. The preferred material for the needles is a polycarbonate processed by a twin-screw extruder to reduce heat degradation of the plastic.

Figure 13:
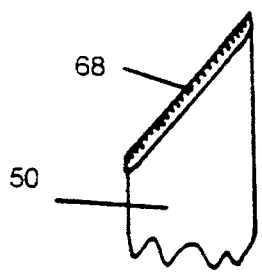
FIGS. 13 through 17 are elevational side views of frangibly sealed hollow needle tips.
Figure 14:
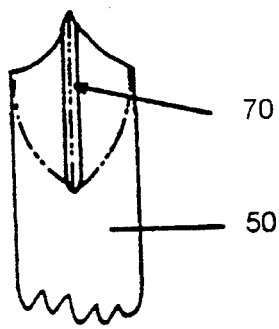
Figure 15:
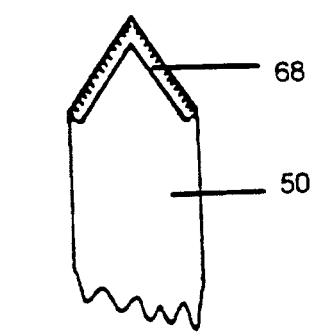
Figure 16:
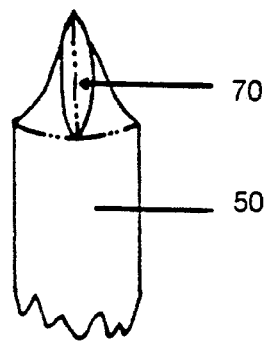
Figure 17:
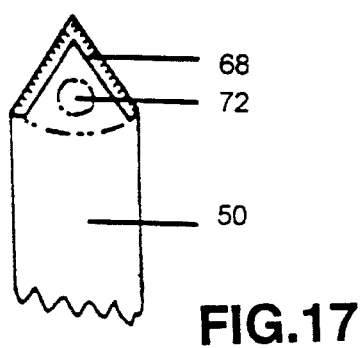

FIGS. 13 through 17 show various frangibly sealed polymeric hypodermic needle tip designs. FIG. 13 shows a frangibly sealed needle tip with an oblique angle. FIG. 14 shows a different elevational view of FIG. 13. FIG. 15 shows a frangibly sealed polymeric hypodermic needle tip with a compound angle. FIG. 16 shows a different elevational view of FIG. 15. The needle tip is pinched together and frangibly fused, glued or solvent welded and cut. The frangibly sealed needle tip (68) is frangibly sealed at junction (70). In the frangible fusing process, heat in the form of a laser or other heat source is applied as the polymeric hypodermic needle (50) is being pinched together. The width and depth of the seal and, therefore, the strength of the seal can be controlled by the length of time, amount of pressure and degree of heat that is applied to the needle. Different plastics require different combinations of time, pressure and heat. Thickness of the needle wall in relation to needle diameter plays an important part. The laser can also perform the cutting process or the needle can be cut with a mechanical process such as shearing. In the gluing or solvent welding process, pinching pressure is maintained while the adhesive or solvent is applied and allowed to cure. Again, length of time and pressure as well as adhesive or solvent applied determine the strength of the breakably sealed needle tip. In FIG. 17, circular area (72) has been weakened by a laser that has reduced the thickness by melting or burning the polymeric material in that area. The frangible seal which is created at junction (70) or weakened circular area (72) is such that it will break or open when sufficient internal pressure is exerted within the polymeric hypodermic needle (50) during the injection process by the medicament being forced out of the syringe or ampule.

FIGS. 20 through 27 illustrate how the piercing member is attached to the supporting base structure. Either the lancet (40) or the needle (50) is attached by adhesive, solvent, heat or the supporting base structure (48) is molded around the piercing member at the attachment zone (74). The heat for bonding at the attachment zone (74) can be supplied by a heat source such as a laser. The attachment zone (74) also can represent the place where the supporting base structure (48) is molded around the piercing member. In the case of molding, the supporting base structure can be molded from one or more parts. The piercing member is attached to the walls of the hole which is sized to receive it in the supporting base structure.

Figure 20:
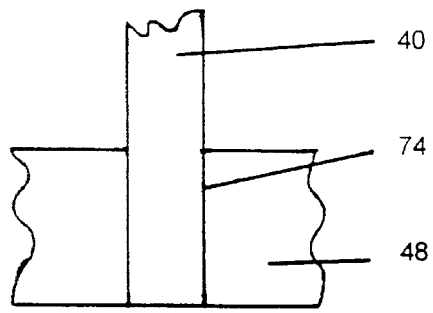
FIGS. 20 through 23 are schematical side views of different means of attaching a lancet to a supporting base structure.
Figure 22:
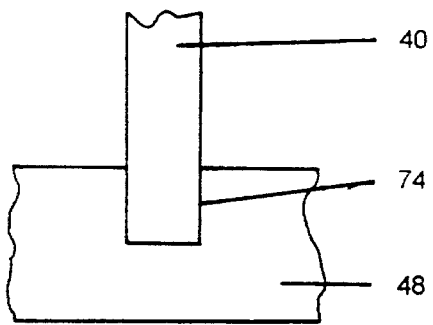
Figure 21:
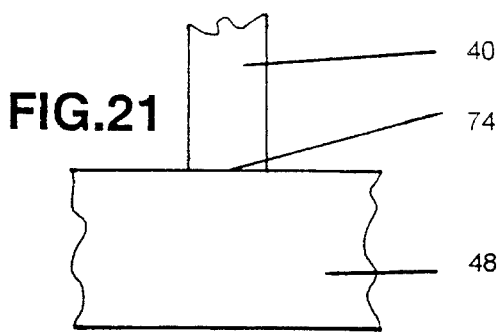
Figure 23:
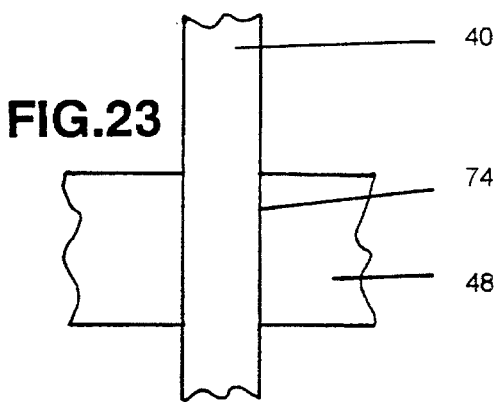

FIGS. 20 through 23 show polymeric hypodermic lancets attached to a supporting base structure. In FIG. 20 the polymeric hypodermic lancet (40) extends completely through the supporting base structure (48) and is flush with the opposite side. In FIG. 23 the polymeric hypodermic lancet (40) extends past the opposite side of the supporting base structure (48). In FIG. 22 the polymeric hypodermic lancet (40) is attached to the walls of a hole which is sized to to receive it in the supporting base structure (48). In FIG. 21 the polymeric hypodermic lancet (40) is attached to the surface of the supporting base structure (48). FIG. 21 is the only one of the four FIGS. where molding is not an option for the means of attachment.

Figure 24:
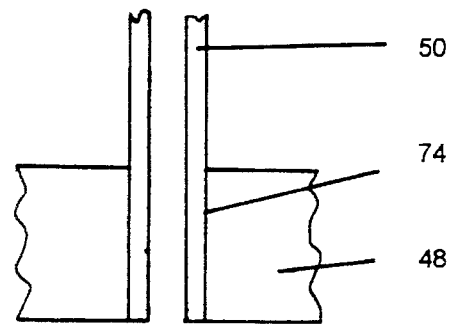
FIGS. 24 through 27 are schematical side views of different means of attaching a hollow needle to a supporting base structure.
Figure 26:
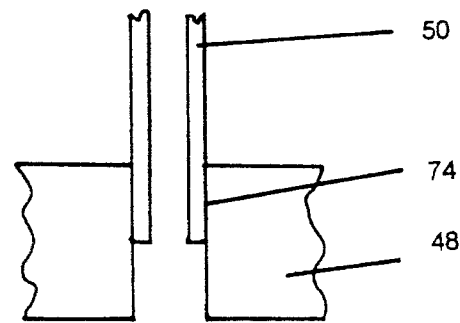
Figure 25:
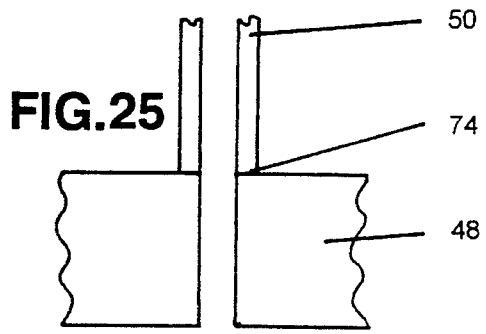
Figure 27:
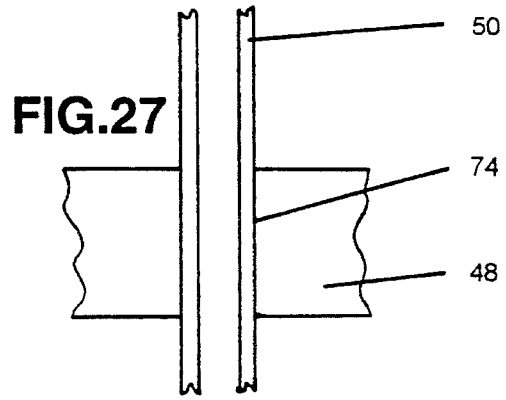

In FIGS. 24 through 27 a polymeric hypodermic needle (50) is attached to the supporting base structure (48) at the attachment zone (74) and a lumen extends completely through the base. The means of attachment is as stated above. FIG. 24 shows a polymeric hypodermic needle (50) extending through the supporting base structure (48) so that the needle is flush with the opposite side of the base. FIG. 27 shows the polymeric hypodermic needle (50) extending past the opposite side of the supporting base structure. FIG. 26 shows the polymeric hypodermic needle (50) partly within a hole sized to receive it in the supporting base structure. FIG. 25 illustrates the polymeric hypodermic needle (50) attached to the surface of the supporting base structure (48) so that the lumen of the needle corresponds with a hole in the base. FIG. 25 is the only one of the four FIGS. in which molding is not an option for the means of attachment of the needle to the base.

These augmented polymeric hypodermic devices will make all hypodermic functions less painful and more safe. They will be cheaper to produce and easier to dispose. They will be a revolutionary change in a field that has not changed in over 100 years.

The foregoing description of the preferred embodiments of the invention has been presented for the purpose of illustration and description. It is not intended to be exhaustive or to limit the invention to the precise form disclosed. Many modifications and variations are possible in the light of the above teaching. It is intended that the scope of the invention be limited not by this detailed description, but rather by the claims appended hereto.

I claim:

1. A hypodermic device for performing a piercing process comprising:

a flexible polymeric piercing member and an augmenting means at least partly about said piercing member and includes a resilient foam at least partly about said piercing member and a guard at least partly about said foam wherein said augmenting means provides such stiffness to said piercing member in order for said piercing member to perform the piercing process.

2. The hypodermic device for performing the piercing process of claim 1 wherein said piercing member is a lancet.

3. The hypodermic device for performing the piercing process of claim 1 wherein said augmenting means further comprises a slidable guard which is at least partly about said foam and in slidable relationship with said member.

4. The hypodermic device of claim 3 wherein said piercing member is a lancet.

5. A hypodermic device for performing a piercing process comprising:

a flexible polymeric piercing member having a piercing tip and an augmenting means which is at least partly about and is in slidable relationship with said piercing member and includes a resilient foam at least partly about and slidably engaged with said piercing member and a guard at least partly about said foam and in slidable relationship with said piercing member wherein said augmenting means provides such stiffness to said piercing member in order for said piercing member to perform the piercing process.

6. The hypodermic device of claim 5 wherein said piercing member is a lancet.

7. A hypodermic device for performing a piercing process comprising:

a flexible polymeric piercing member with a piercing tip;

and an augmenting means at least partly about said piercing member and includes a resilient foam at least partly about said piercing member and a guard at least partly about said foam wherein said augmenting means provides such stiffness to said piercing member in order for said piercing member to perform the piercing process.

8. The hypodermic device of claim 7 wherein said piercing member is a lancet.

9. The hypodermic device of claim 7 wherein said guard is in slidable relationship with said piercing member.

10. The hypodermic device of claim 9 wherein said piercing member is a lancet.

* * * * *